United States Patent [19]

Morsdorf et al.

[11] Patent Number: 5,108,998
[45] Date of Patent: Apr. 28, 1992

[54] CARDIOTONIC THIADIAZINE DERIVATIVES

[75] Inventors: Peter Morsdorf, Langenzenn; Heidrun Engler, Cadolzburg; Reinhold Weidner, Nuremberg; Rolf Herter, Zeitlarn; Kurt-Henning Ahrens, Nuremberg, all of Fed. Rep. of Germany

[73] Assignee: Heumann Pharma GmbH & Co., Fed. Rep. of Germany

[21] Appl. No.: 512,812

[22] Filed: Apr. 23, 1990

[30] Foreign Application Priority Data

Apr. 25, 1989 [DE] Fed. Rep. of Germany ....... 3913597

[51] Int. Cl.⁵ ................. C07D 285/16; C07D 417/12; C07D 417/14; A61K 31/54
[52] U.S. Cl. ................. 514/222.5; 514/218; 544/8; 540/575
[58] Field of Search ................ 544/8; 514/222.5, 218; 540/575

[56] References Cited

U.S. PATENT DOCUMENTS 4,591,591  5/1986  Robertson ..................... 514/254

FOREIGN PATENT DOCUMENTS 0052442  5/1982  European Pat. Off. .
0075436  3/1983  European Pat. Off. .
0220044  4/1987  European Pat. Off. .
0303418  2/1989  European Pat. Off. .
0304534  3/1989  European Pat. Off. .
0339208  11/1989  European Pat. Off. .
2837161  3/1980  Fed. Rep. of Germany .

OTHER PUBLICATIONS

*J. Med. Chem.* 28: 1414–1422 "The Histamine H₂ Receptor Agonist Impromidine: Synthesis and Structure–Activity Considerations", G. J. Durant et al.

Primary Examiner—John M. Ford
Attorney, Agent, or Firm—Burns, Doane, Swecker & Mathis

[57] ABSTRACT

New diazine derivatives corresponding to the general formula I

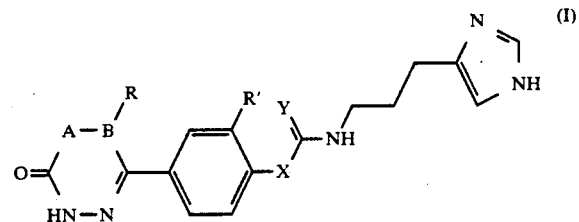

and the physiologically acceptable salts thereof are described. The compounds according to the invention are new positive inotropic compounds having a higher and/or more selective action than compounds hitherto known and are therefore suitable for the treatment and prevention of diseases of the heart and circulation.

19 Claims, No Drawings

CARDIOTONIC THIADIAZINE DERIVATIVES

Digitalis glycosides such as digoxin and digitoxin and sympathomimetic drugs have for many decades been the only therapeutic means available for the treatment of cardiac insufficiency. The marked disadvantages of both groups of substances, such as narrow therapeutic range, tachyphylaxis and insufficient availability in forms suitable for oral administration led to an intensive search for other classes of substances having a positive inotropic action.

Pyridazinone derivatives such as pimobendan (DE-OS-28 37 161), imazodan (EP-OS 0 75 436) and indolidan (U.S. Pat. No. 4,591,591) proved to serve as alternatives by virtue of their good contractility enhancing action. Bioisosteric groups of compounds such as thiadiazinones and triazinones (EP-OS-0 52 442) have also been described as having similar pharmacological properties.

Histamine-$H_2$-agonists, on the other hand such as impromidin (J. Med. Chem. 28, 1414 (1985)) constitute another interesting group of cardiotonic substances whose action is based on a mechanism different from that of the pyridazinone derivatives.

It is an object of the present invention to provide new positive inotropic compounds having a higher and/or more selective activity than the compounds known at present. This object is fulfilled by the present invention.

The invention therefore relates to diazine derivatives corresponding to the general formula I

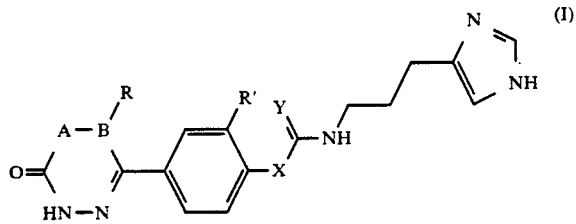

wherein A stands for a sulphur atom and B stands for carbon atom or one of the two atoms denoted by A and B is an unsubstituted nitrogen atom or a nitrogen atom substituted with a $C_1$-$C_3$-alkyl group while the other of the two atoms is a carbon atom, R denotes a hydrogen atom, a $C_1$-$C_3$-alkyl group or a hydroxymethyl group and R' denotes a hydrogen atom, a nitro group, a cyano group or a halogen atom, X stands for one of the groups denoted by the following formulae

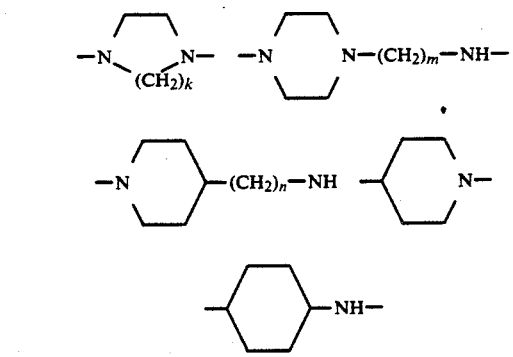

—NH(CH$_2$)$_m$—NH—, —O(CH$_2$)$_n$—NH— and —(CH$_2$)$_n$—NH—, wherein k has the value 2 or 3, m has the value 2,3,4,5 or 6 and n has the value 0,1,2 3 or 4, Y stands for an oxygen atom or one of the following groups

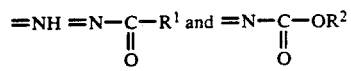

wherein $R^1$ stands for a straight chain or branched chain $C_1$-$C_6$-alkyl group or for an aryl group optionally substituted by one or more halogen atoms, $C_1$-$C_3$-alkyl groups or $C_1$-$C_3$-alkoxy groups and $R^2$ stands for a straight chain or branched chain $C_1$-$C_4$-alkyl group optionally substituted with one or more halogen atoms, $C_1$-$C_3$-alkoxy groups or phenyl groups, and to the physiologically acceptable salts thereof.

In the general formula I, A denotes a sulphur atom and B a carbon atom or one of the two atoms denoted by A and B stands for a nitrogen atom which is unsubstituted or substituted with a $C_1$-$C_3$-alkyl group and the other of the two atoms is a carbon atom. The methyl, ethyl and n-propyl group are examples of $C_1$-$C_3$-alkyl groups, the methyl group being preferred.

R stands for a hydrogen atom, a $C_1$-$C_3$ alkyl group or a hydroxymethyl group. The $C_1$-$C_3$-alkyl group has the meaning defined above, the methyl group again being preferred. R' denotes a nitro group, a cyano group or a halogen atom, for example, a fluorine, chlorine or bromine atom, preferably a fluorine atom, but compounds in which R' stands for a nitro group or a cyano group are particularly preferred.

X stands for the following groups:

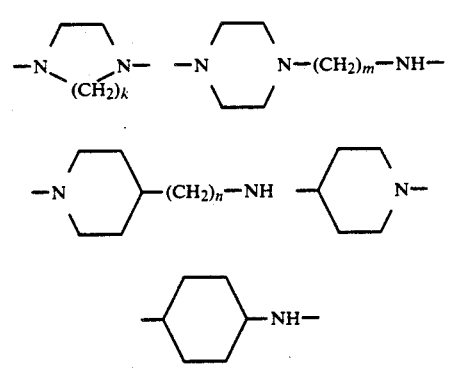

—NH(CH$_2$)$_m$N—, 'O(CH$_2$)$_n$NH— or (CH$_2$)$_n$NH—, wherein the index k has the value 2 or 3 the value 2 being preferred. The index m has the value 2, 3, 4, 5 or 6, the values 2, 3 and 4 being preferred n stands for an integer with a value from 0 to 4. Y stands for an oxygen atom or for a group corresponding to one of the following formulae:

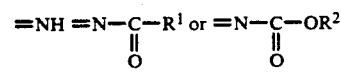

wherein $R^1$ stands for a straight chain or branched chain $C_1$-$C_6$-alkyl group, preferably a $C_1$-$C_3$-alkyl group, or for an aryl group optionally mono-, di- or trisubstituted with halogen atoms, $C_1$-$C_3$-alkyl groups or $C_1$-$C_3$-alkoxy groups, monosubstitution being preferred, in particular in the para-position.

The methyl, ethyl, n-propyl, i-propyl, n-butyl and i-butyl group are examples of $C_1$-$C_6$-alkyl group. The aryl group may be, for example, a phenyl or naphthyl group, the phenyl group, being preferred. Examples of halogen atoms and $C_1$-$C_3$-alkyl groups forming substituents for the aryl group are those listed above in connection with groups R and R'. The methoxy, ethoxy and n-propoxy group are examples of $C_1$-$C_3$-alkoxy groups which also constitute substituents on the aryl group.

$R^2$ is a straight chain or branched chain $C_1$-$C_4$-alkyl group which may be unsubstituted or substituted with one or more halogen atoms, $C_1$-$C_3$-alkoxy groups or phenyl groups. The methyl, ethyl, n-propyl, i-propyl, n-butyl, i-butyl and tert.-butyl groups are examples of $C_1$-$C_4$-alkyl group, methyl, ethyl and tert.-butyl groups being preferred. When $R^2$ is substituted with one of the above-mentioned substituents, mono-substitution is preferred, in particular on the terminal carbon atom. The fluorine, chlorine and bromine atoms are again examples of halogen atoms as substituents on the $C_1$-$C_4$-alkyl group, the fluorine and chlorine atoms being preferred. The methoxy, ethoxy and n-propoxy groups are examples of $C_1$-$C_3$-alkoxy groups which may also serve as substituents on the $C_1$-$C_4$-alkyl group denoted by $R^2$, the methoxy and ethoxy group being preferred.

Y preferably denotes a group corresponding to one of the following formulae

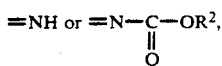

the group $=NH$ being particularly preferred and $R^2$ having the meaning defined above and preferably standing for an ethyl or a tert.-butyl group.

A preferred group of compounds according to the invention is characterised in that A stands for a sulphur atom and B for a carbon atom, R stands for a hydrogen atom, a $C_1$-$C_3$-alkyl group or a hydroxymethyl group and R' for a hydrogen atom, a nitro group, a cyano group or a halogen atom, X stands for a group corresponding to one of the following formulae:

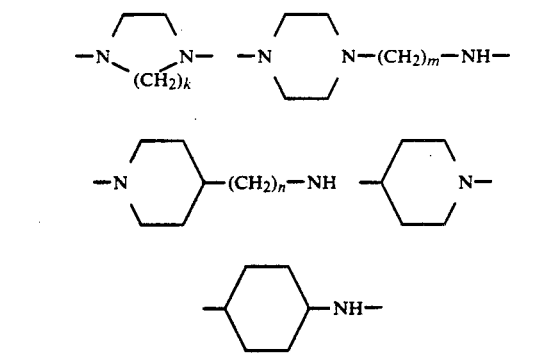

—NH(CH$_2$)$_m$—NH—m, —O(CH$_2$)$_n$—NH— and —(CH$_2$)$_n$—NH—, wherein k has the value 2 or 3, m has the value 2,3,4,5 or 6, n has the value 0,1,2,3 or 4 and Y stands for the group $=NH$.

Another preferred group of compounds according to the invention is characterised in that A stands for a nitrogen atom or the group —N—CH$_3$ and B stands for a carbon atom, R stands for a hydrogen atom or a $C_1$-$C_3$-alkyl group and R' stands for a hydrogen atom, a nitro group, a cyano group or a halogen atom, and Y stands for the group $=NH$. Those compounds of this group in which R stands for a methyl group and R' for a nitro group are particularly preferred.

Another preferred group of compounds according to the invention is characterised in that A stands for a carbon atom and B for a nitrogen atom. R denotes a hydrogen atom or a methyl group. R' denotes a hydrogen atom, a nitro group, a cyano group or a halogen atom and Y stands for the group $=NH$.

The specific compounds mentioned below are particularly preferred:

5-[4-[4-[3-(1H-Imidazol-4-yl)propylamino-iminomethylene]-piperazin-1-yl]-3-nitrophenyl]-6-methyl-3H,6H-1,3,4-thiadiazin-2-one and the physiologically acceptable salts thereof.

$N^1$-[3-(1H-Imidazol-4-yl)propyl]-$N^3$- [1-[4-(6-methyl-2-oxo-3,6-dihydro-1,3,4-thiadiazin-5-yl)-2-nitro-phenyl]piperidin-4-yl]-guanidine and the physiologically acceptable salts thereof.

5-[4-[4-[3-(1H- yl)propylamino-iminomethylene]-piperazin-1-yl]-3-nitro-phenyl]-3H,6H-1,3,4-thiadiazin-2-one and the physiologically acceptable salts thereof.

$N^1$-[3-(1H-Imidazol-4-yl)propyl]-$N^3$-[1-[4-(2-oxo-3,6-dihydro-1,3,4-thiadiazin-5-yl)-2-nitro-phenyl]-piperidin-4-yl]-guanidine and the physiologically acceptable salts thereof.

The compounds according to the invention may be prepared by the following method:

Compounds corresponding to the general formula I in which A, B, R, R' and X have the meanings indicated above and Y stands for one of the following groups:

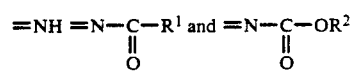

wherein $R^1$ and $R^2$ have the meanings defined above may be prepared by reacting a compound corresponding to the general formula II

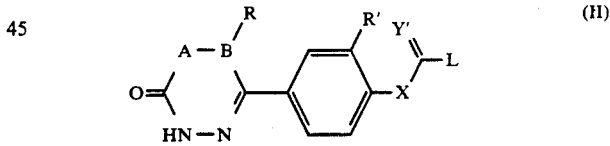

wherein A, B, R, R', X and Y are defined as above L stands for a $C_1$-$C_4$-alkylthio, a phenylthio, a $C_1$-$C_4$-alkoxy or a phenoxy group, with a compound corresponding to formula (III)

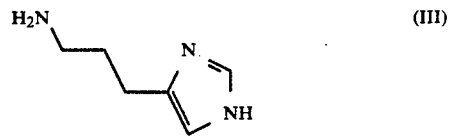

to form a compound corresponding to the general formula I.

The above group of compounds may also be prepared by reacting a compound corresponding to the general formula IV

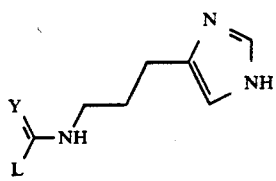 (IV)

wherein Y and L have the meanings given in the description of the first process with a compound corresponding to the general formula V

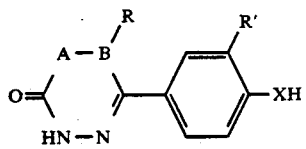 (V)

wherein A, B, R, R' and X have the meanings defined above.

In both process variations, the removable groups L in the compounds corresponding to formulae II and IV are preferably $C_1$–$C_4$-alkylthio groups in particular the methylthio group, or a phenoxy group. The compounds corresponding to the general formulae II and IV are preferably put into the process in a ratio of from 1:1 to 0.8:1, more preferably in equimolar quantities, based on the compounds corresponding to the general formula III or V. The reactions are carried out in a polar solvent such as acetonitrile, pyridine, dimethylformamide or an alcohol, preferably a secondary or tertiary alcohol, e.g. isopropanol, and at temperatures from 20° C. to the reflux temperature of the solvent used.

Compounds corresponding to the general formula I in which A, B, R, R' and X have the meanings defined above and Y stands for the group =NH may also be prepared by acid or alkaline hydrolysis and if necessary decarboxyation of a compound corresponding to the general formula Ia

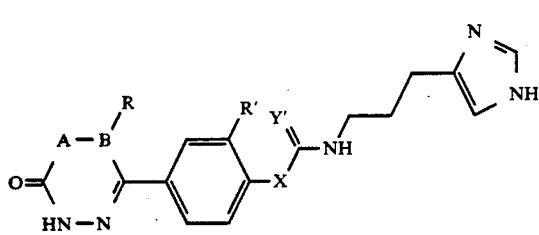 (Ia)

wherein A, B, R, R' and X have the meanings indicated above and Y' stands for one of the following groups

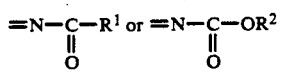

wherein $R^1$ and $R^2$ have the meanings indicated above, to form a compound corresponding to the general formula I in which Y stands for the group =NH.

Acid hydrolysis may be carried out, for example, in an aqueous mineral acid such as hydrochloric or hydrobromic acid or sulphuric acid and at temperatures from 20° to 100° C. but it may in some cases be preferable to employ non-aqueous reaction conditions, for example when Y' stands for the group

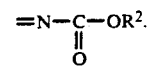

These milder methods, which are preferably carried out at room temperature, include, for example, solvolysis with trifluoroacetic acid in a chlorinated hydrocarbon such as dichloromethane or chloroform or a reaction with hydrobromic acid in glacial acetic acid.

Alkaline hydrolysis is carried out in a dilute solution of alkali metal or alkaline earth metal carbonates or alkali metal or alkaline earth metal hydroxides in water, lower alcohols or mixtures of the two and at temperatures ranging from room temperature to the reflux temperature of the solvent used.

Compounds according to the invention corresponding to the general formula I in which A, B, R, R' and X have the meanings indicated above and Y stands for an oxygen atom may be prepared from a compound corresponding to the general formula VI

 (VI)

wherein Z stands for a halogen atom, a trichloromethoxy group or the residue of an azole or benzazole which has at least two nitrogen atoms in the 5-membered ring and is attached via a nitrogen atom, by reacting this compound successively with a compound corresponding to the general formula V

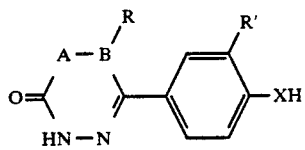 (V)

wherein A, B, R, R' and X have the meanings defined above and with a compound corresponding to the general formula III

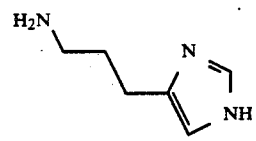 (III)

The reactions of compounds corresponding to the general formula VI with compounds of formulae V and III may be carried out in any sequence but the compound of formula VI is preferably first reacted with a compound of formula V and then with the compound of formula III. The reactions are normally carried out as one-shot reactions, i.e. the intermediate stages are neither isolated nor purified.

Examples of azoles and benzazoles denoted by Z include the imidazole, the 1,2,4-triazole, the tetrazole, the benzimidazole and the benzotriazole ring. N,N'-Carbonyldiimidazole is a preferred compound corresponding to the general formula VI. The reactions are carried out in an inert solvent. e.g. a halogenated hydrocarbon such as dichloromethane, an ether. e.g. tetrahydrofuran, or a polar solvent such as acetonitrile or dimethylformamide. The reaction temperatures may lie in the range from −20° C. to the boiling point of the solvent. When Z in the general formula VI stands for a halogen atom, it is advisable to use an acid acceptor, e.g. a tertiary amine such as trimethylamine or pyridine.

The compounds obtained by the various process variations are isolated and purified in the usual manner, for example by recrystallisation, chromatographic methods, etc. The compounds obtained from the various process variations may be converted into their physiologically acceptable salts, e.g. with mineral acids such as hydrochloric acid, hydrobromic acid, hydriodic acid, phosphoric acid, metaphosphoric acid, nitric acid or sulphuric acid, or with organic acids such as formic acid, acetic acid, propionic acid, phenylacetic acid, tartaric acid, citric acid, fumaric acid, methane sulphonic acid, embonic acid, etc.

The compounds according to the invention corresponding to the general formula I may be present in various tautomeric forms and several stereoisomeric forms. The invention therefore covers not only the salts and hydrates of the above described compounds corresponding to the general formula I but also all tautomeric and stereoisomeric forms thereof.

The compounds according to the invention may be formulated as desired for administration.

The invention therefore also covers medicaments containing at least one compound according to the invention for use in human or veterinary medicine. Such medicaments may be prepared conventionally with the aid of one or more pharmaceutically acceptable carriers or diluents.

The compounds according to the invention may therefore be formulated for oral, buccal, topical, parenteral or rectal administration.

For oral administration, the medicament may be provided, for example, in the form of tablets, capsules, powders, solutions, syrups or suspensions prepared by conventional methods using acceptable diluents. For buccal administration, the medicament may be provided in the form of conventionally formulated tablets or sachets.

The compounds according to the invention may be formulated for parenteral administration by bolus injection or continuous infusion. Formulations for injection may be provided in the form of ampoules containing single doses or they may be provided in multiple dose containers with added preservative. The medicaments may assume forms such as suspensions, solutions or emulsions in oily or aqueous carriers and may contain formulation auxiliaries such as suspending, stabilizing and/or dispersing agents.

Alternatively, the active ingredient may be provided in powder form to be reconstituted before use with a suitable carrier, e.g. sterile, pyrogen-free water.

The compounds according to the invention may also be formulated for rectal preparations such as suppositories or retention enemas which may contain e.g. conventional suppository excipients such as cocoa butter or other glycerides.

For topical use, the compounds according to the invention may be formulated in the conventional manner as ointments, creams, gels, lotions, powders or sprays.

For oral administration, a suitable daily dose of compounds according to the invention is 1 to 4 doses of up to a total of 5 mg to 1 g per day, depending on the patient's condition. In individual cases it may be necessary to deviate from the stated quantities, depending on the individual response to the active ingredient or the nature of its formulation and the time or time interval at which the doses are administered. Thus, for example, it may in certain cases be sufficient to use less than the minimum quantity stated above while in other cases it may be necessary to exceed the upper limit.

The diazine derivatives according to the invention corresponding to the general formula I manifest marked cardiovascular, in particular cardiotonic effects and are therefore suitable for the treatment and prevention of diseases of the heart and circulation.

Thus they manifest an excellent positive inotropic action on narcotized guinea-pigs after intravenous administration.

Haemodynamic Characterisation in narcotized guinea-pigs (i.v. administration)

a) Method

The animals are narcotized with urethane (1.5 g/kg). The trachea is canulated for volume controlled breathing. The two carotid arteries are then exposed operatively. A tip catheter (3F) is introduced via the right carotid artery and is moved forwards through the ascending aorta into the left ventricle while the pressure is continuously recorded. Successful passage through the aortic valves is recognized by the typical left ventricular pressure curve. A thermistor probe (3F, F. Edwards) is pushed forwards into the aortic arc via the left carotid for thermodilution. The thermistor probe also has a lumen for recording the arterial blood pressure. A catheter is passed through the right jugular vein to be placed in front of the right atrium for introduction of the cold injection (0.2 ml of 0.9 % NaCl, 15° C.).

All the substances are dissolved in physiological saline solution and are infused via the left jugular vein (infusion volume 0.02 ml/min); the substances are applied after haemodynamic stabilization and under $\beta$-blockage (Metoprolol 2 mg/kg i.m.). All parameters of the circulation are continuously recorded on a direct recording apparatus. The contractility (dp/dt) is calculated from the volume curve.

b) Results of measurements

| Example No. | Dose µg/kg/min | Maximum increase in contractility LV dp/dt |
|---|---|---|
| 1 | 5.0 | +193% |
| 2 | 10.0 | +126% |
| 3 | 10.0 | +96% |

The following Examples illustrate the invention.

All intermediate products were routinely checked for purity by thin layer chromatography, using UV light and spray reagents such as True Blue salt B/sodium hydroxide solution for detection.

Thin layer chromatography was carried out on silica gel films Polygram SIL G/UV$_{254}$ (Machery-Nagel). The preparative chromatography was carried out using silica gel Merck Art.No. 7734 and 7749.

The following abbreviations were used for the solvents:

| | | |
|---|---|---|
| A | Dichloromethane:methanol | 80:20 |
| B | Ethyl acetate:methanol:conc.ammonia | 80:18:2 |
| C | Dichloromethane:methanol:conc.ammonia | 85:13:2 |

| | | |
|---|---|---|
| D | Dichloromethane:methanol:conc.ammonia | 60:30:10 |
| E | Ethyl acetate:buffer* | 60:40 |
| F | Ethyl acetate:buffer* | 50:50 |
| G | Dichloromethane:methanol | 90:10 |
| H | Dichloromethane:methanol:conc.ammonia | 90:9:1 |
| I | Dichloromethane:acetonitrile | 90:10 |

*Buffer: Methanol:conc.ammonia saturated with ammonium chloride 95:5

Preparation of the starting compound 5-(4-Chloro-3-nitro-phenyl)-6-methyl-3H,6H-1,3,4-thiadiazin-2-one 22 g of a 23% solution of hydrogen chloride in isopropanol are added to 29.3 g (100 mmol) of α-bromo-4-chloro-3-nitropropiophenone and 14.2 g (134 mmol) of hydrazine-thiocarboxylic acid methyl ester in 400 ml of absolute ethanol and the reaction mixture is boiled under reflux for 3.5 hours. The resulting solution is then concentrated to about 100 ml by evaporation in vacuo and cooled to 2° C. in an ice bath. The precipitated solid is suction filtered and dried in vacuo. A second fraction is obtained by further concentration of the mother liquor by evaporation and dilution with 50 ml of dichloromethane. The total yield is 25.6 g (90%) of pale yellow crystals, m.p. 168°–169° C. $C_{10}H_8ClN_3O_3S$ (285.71)

EXAMPLE 1

$N^1$-[3-(1H-Imidazol-4-yl)propyl]-$N^3$-2-[4-(6-methyl-2-oxo-3,6-dihydro-1,3,4-thiadiazin-5-yl)-2-nitro-phenyl]amino]ethyl]-guanidine

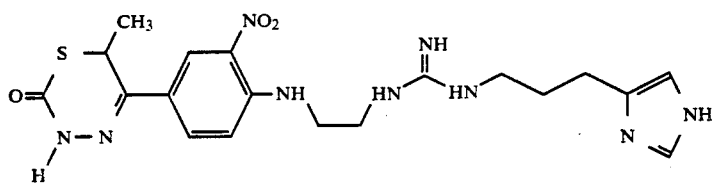

a) 5-[4-(2-Aminoethyl)amino-3-nitro-phenyl]-6-methyl-3H,6H-thiadiazin-2-one

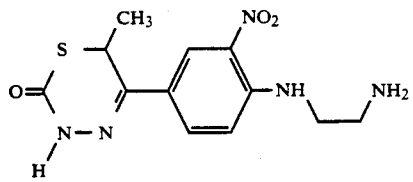

5.7 g (20 mmol) of 5-(4-chloro-3-nitro-phenyl)-6-methy-3H,6H-1,3,4-thiadiazin-2-one and 4.0 ml (60 mmol) of ethylene diamine are boiled under reflux in 40 ml of dioxane for 2 hours.

When the reaction mixture has cooled down, it is added to a solution of 2 g of potassium carbonate in 50 ml of water and the aqueous phase is extracted three times with 30 ml portions of chloroform/methanol (80/20 v/v). The oil obtained after drying and concentration of the combined organic phases by evaporation in vacuo is chromatographed on silica gel with solvent A and yields 1.82 g (26%) of orange yellow crystals, m.p. 165°–168° C., after concentration of the main fraction by evaporation and crystallisation of the residue from methanol/water.

$C_{12}H_{15}N_5O_3S$ (309.35)
Rf=0.27 (Solvent B)

b) S-Methyl-N-[2-[[4-(6-methyl-2-oxo-3,6-dihydro-1,3,4-thiadiazin-5-yl)-2-nitro-phenyl]-amino]ethyl]-isothiuronium iodide

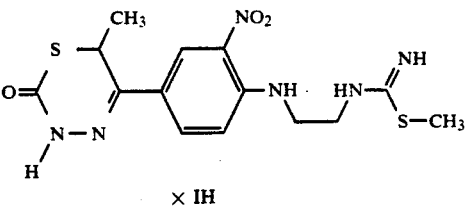

1.40 g (4.5 mmol) of 5-4-(2-aminoethyl)amino-3-nitro-phenyl]-6-methyl-3H,6H-thiadiazin-2-one and 1.24 g (5 mmol) of dithiocarbamic acid-S,S-dimethylester-hydriodide are boiled under reflux in 60 ml of acetonitrile for 8 hours.

The crude product obtained after removal of the solvent by evaporation in vacuo is chromatographed on silica gel with solvent A and after concentration of the main fraction by evaporation in vacuo it yields 1.62 g (71%) of an orange yellow, amorphous solid.

$C_{14}H_{19}N_6O_3S_2$(510.38)
Rf=0.38 (Solvent C)

c) $N^1$-[3-(1H-Imidazol-4-yl)propyl]-$N^3$-[2-[[4-(6-methyl-2-oxo-3,6-dihydro.1,3,4-thiadiazin-5. yl)-2-nitro-phenyl]amino]ethyl]-guanidine 1.60 g (3.13 mmol) of the isothiuronium iodide obtained under b) and 0.395 g (3.13 mmol) of 3-(1H-imidazol-4-yl)propylamine are stirred in 30 ml of dimethylformamide for 3 days at room temperature. The reaction mixture is concentrated by evaporation in vacuo. 20 ml of a 20% potassium carbonate solution are then added and the reaction mixture is extracted with 3×30 ml of a chloroformmethanol mixture (80/20 v/v). The combined organic phases are dried, filtered and concentrated by evaporation in vacuo.

After the crude product has been chromatographed twice on silica gel with solvents D and E, 0.15 g (10%) of an orange red, amorphous powder having an unsharp melting point at 135°–145° C. is obtained.

$C_{19}H_{25}N_9O_3S$ (459.53)
Rf=0.48 (Solvent F)

| $^1$H NMR data (DMSO-$d_6$, TMS as internal standard) | δ = 1.37 | (d) | 3H |
|---|---|---|---|
| | 1.68 | (quin) | 2H |
| | 2.45 | (m) | 2H |
| | 2.9–3.6 | (m) | 6H |
| | 4.64 | (q) | 1H |
| | 6.69 | (s) | 1H |
| | 7.19 | (d) | 1H |
| | 7.45 | (s) | 1H |
| | 7.93 | (dd) | 1H |
| | 8.36 | (d) | 1H |
| | 8.6 | (broad) | 5H, replaceable by $D_2O$ ppm. |

EXAMPLE 2

$N^1$-[3-(1H-Imidazol-4-yl)propyl]-$N^3$-[3-[[4-(6-methyl-2-oxo-3,6-dihydro-1,3,4-thiadiazin-5-yl)-2-nitro-phenyl]amino]propyl]-guanidine

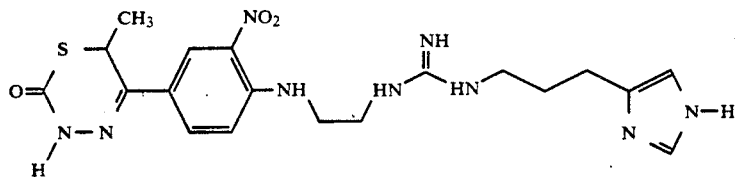

a) 5-[4-(3-Aminopropyl)amino-3-nitro-phenyl)]-6-methyl-3H,6H-1,3,4-thiadiazin-2-one 7.27 g (75%) of an orange red solid melting at 192°–193° C. are obtained analogously to Example 1a) from 8.57 g (30 mmol) of 5-(4-chloro-3-nitro-phenyl)-6-methyl-3H.6H-1,3,4-thiadiazin-2-one and 7.5 ml (90 mmol) of 1,3-diaminopropane.

$C_{13}H_{17}N_5O_3S$ (323.38)

Rf=0.43 (Solvent C)

b) S-Methyl-N-[3-[[4-(6-methyl-2-oxo-3,6-dihydro-1,3,4-thiadiazin-5-yl)-2-nitro-phenyl]amino]propyl]-isothiuronium iodide 1.4 g (53%) of an orange red, amorphous solid are obtained by a method corresponding to that of Example 1b) from 1.60 g (5 mmol) of 5-[4-(3-aminopropyl)amino-3-nitro-phenyl]-6-methyl-3H,6H-1,3,4-thiadiazin-2-one and 1.37 g (5.5 mmol) of dithiocarbamic acid-S,S-dimethylester hydroiodide.

$C_{15}H_{21}IN_6O_3S_2$ (524.41)

Rf=0.4 (Solvent A)

c) $N^1$-[3-(1H-Imidazol-4-yl)propyl]-$N^3$-[3-[[4-(6-methyl-2-oxo-3,6-dihydro-1,3,4-thiadiazin-5-yl)-2-nitro-phenyl]amino]propyl]-guanidine The title compound is obtained from 1.26 g (2.5 mmol) of the isothiuronium salt obtained under b) and 0.32 g (2.6 mmol) of 3-(1H-imidazol-4-yl)-propylamine in a manner analogous to EXAMPLE 1C).

The chromatographically purified product crystallises from ethanol as a brick red solid in a yield of 0.21 g (18%) and with a melting range of 139°–143° C.

$C_{20}H_{27}N_9O_3S$ (473.56)

Rf=0.44 (Solvent F)

| $^1$H-NMR data (DMSO-$d_6$. TMS as internal standard) | δ = | 1.37 | (d) | 3H |
|---|---|---|---|---|
| | | 1.61–1.96 | (m) | 4H |
| | | 2.48 | (t) | 2H |
| | | 3.0–3.6 | (m) | 6H |
| | | 4.55 | (q) | 1H |
| | | 6.72 | (s) | 1H |
| | | 7.12 | (d) | 1H |
| | | 7.50 | (s) | 1H |
| | | 7.92 | (dd) | 1H |
| | | 8.38 | (d) | 1H |
| | | 8.5 | (broad) | 5H, replaceable by D$_2$O ppm. |

EXAMPLE 3

5-[4-[4-[3-(1H-Imidazol-4-yl)propylamino-iminomethylene]piperazin-1-yl]-3-nitro-phenyl]-6-methyl-3H,6H-1,3,4-thiadiazin-2-one

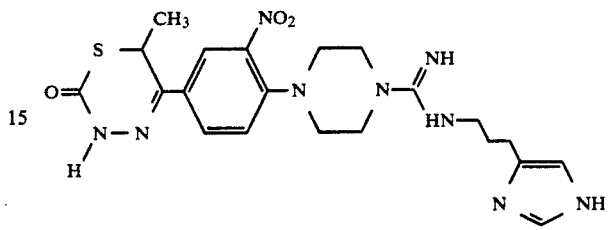

a) 5-(Piperazin-1-yl)-3-nitro-phenyl]-6-methyl-3H,6H-1,3,4-thiadiazin-2-one 9.0 g (31.5 mmol) of 5-(4-chloro-3-nitro-phenyl)-6-methyl-3H,6H-1 3,4-thiadiazin-2-one and 8.1 g (94.4 mmol) of piperazine are boiled under reflux in 50 ml of dioxane for 2 hours.

When the reaction mixture has cooled down, it is filtered, the filtrate is concentrated by evaporation in vacuo and the residue obtained is recrystallised from methanol.

8.6 g (81%) of orange red crystals, m.p. 190°–192° C., are obtained.

$C_{14}H_{17}N_5O_3S$ (335.39)

Rf=0.47 (Solvent C)

b) 5-[4-[4-Methylthio-iminomethylene-piperazin-1-yl]-3nitro-phenyl]-6-methyl-3H,6H-1,3,4-thiadiazin-2-one-hydroiodide 8.0 g (24 mmol) of 5-[4 (Piperazin-1-yl)-3-nitro-phenyl]-6-methyl-3H,6H-1,3,4-thiadiazin-2-one and 9.7 g (39 mmol) of dithiocarbamic acid-S,S-dimethylester-hydroiodide are boiled under reflux in 180 ml of acetonitrile for 13 hours.

After cooling to room temperature, the unreacted starting material is removed by suction filtration and the filtrate is concentrated by evaporation in vacuo. The crude product is chromatographed on silica gel with solvent G and after removal of the solvent by evaporation and crystallisation of the product fractions with ethyl acetate/methanol, it yields 4.25 g (33%) of orange red crystals, m.p. 193°–196° C.

$C_{16}H_{21}IN_6O_3S_2$ (536.42)

Rf=0.62 (Solvent H)

c) 5-[4-[4-[3-(1H-Imidazol-4-yl)propylamino-iminomethylene]-piperazin-1-yl]-3-nitro-phenyl]-6-methyl-3H,6H, 1,3,3-thiadiazin-2-one 2.52 g (4.7 mmol) of the isothiuronium iodide obtained under b) and 0.64 g (5.1 mmol) of 3-(1H-imidazol-4-yl)-propylamine are stirred in 25 ml of dimethylformamide at room temperature for 30 hours.

The reaction mixture is then to a large extent evaporated in vacuo and 20 ml of saturated potassium carbonate solution are added to the residue which is then extracted twice with 50 ml portions of dichloromethane/methanol (80/20 v/v). The combined organic phases are dehydrated with potassium carbonate and concentrated by evaporation in vacuo.

The resulting crude product is chromatographed on silica gel with solvent F. The product fractions are combined, extracted twice with 10% potassium carbonate solution, dehydrated and concentrated by evaporation in vacuo.

0.68 g (30%) of an amorphous, orange yellow solid is obtained after the residue has been stirred up with ethyl acetate.

$C_{21}H_{27}N_9O_3S$ (485.57)
Rf=0.32 (Solvent E)

| $^1$H-NMR data (DMSO-$d_6$, TMS as in internal standard) | δ = | 1.46 | (d) | 3H |
|---|---|---|---|---|
| | | 1.62 | (quin) | 2H |
| | | 2.56 | (t) | 2H |
| | | 3.0–3.8 | (m) | 10H |
| | | 4.79 | (q) | 1H |
| | | 6.79 | (s) | 1H |
| | | 7.39 | (d) | 1H |
| | | 7.55 | (s) | 1H |
| | | 8.01 | (d) | 1H |
| | | 8.25 | (s) | 1H |
| | | 9.5 | (broad) | 3H, replaceable by $D_2O$ ppm. |

EXAMPLE 4

$N^1$-[3-(1H-imidazol-4-yl)propyl]-$N^2$-tert.-butoxycarbonyl-$N^3$-[1-[4-(6-methyl-2-oxo-3,6-dihydro-1,3,4-thiadiazin-5-yl)-2-nitro-phenyl]-piperidin-4-yl]-guanidine

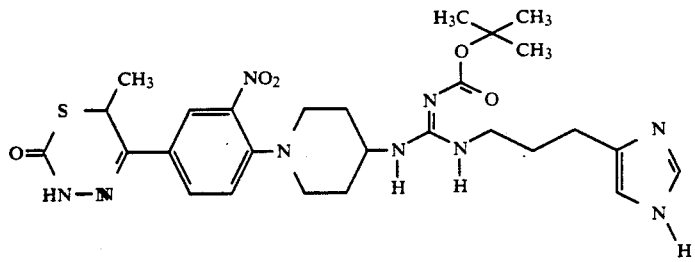

a) 5-[5-(4-Phthalimido-piperidin-1-yl)-3-nitro-phenyl]-6-methyl-3H,6H-1,3,4-thiadiazin-2-one 7.79 g (27.3 mmol) of 5-(4-chloro-3-nitro-phenyl)-6-methyl-3H,6H-1,3,4-thiadiazin-2-one 7.79 g (27.3 mmol) of 5-(4-chloro-3-nitro-phenyl)-6-methyl-3H, 6H-1,3,4-thiadiazin-2one, 6.91 g (30.0 mmol) of 4-phthalimido-piperidine and 4.2 ml (30 mmol) of triethylamine are boiled under reflux in 150 ml of dioxane for 8 hours.

After cooling, the suspension obtained is concentrated by evaporation in vacuo and the residue is taken up in 100 ml of water and stirred for 10 minutes. The resulting solid is separated by suction filtration and dried in vacuo at 75° C.

12.2 g (93%) of orange yellow crystals melting at 267°–269° C. are obtained.

$C_{23}H_{21}N_5O_5S$
Rf=0.50 (Solvent I)

b) 5-[4-(4-Aminopiperidin-1-yl)-3-nitro-phenyl]-6-methyl-3H,6H-1,3,4-thiadiazin-2-one 8 0 g (16.7 mmol) of the phthalimide compound obtained under a) are boiled under reflux with 4.0 ml (83.5 mmol) of hydrazine hydrate in 110 ml of ethanol for one hour.

After cooling to room temperature, the precipitated solid is suction filtered and the filtrate is concentrated by evaporation in vacuo. The residue obtained is stirred into 100 ml of water and the solid thus precipitated is suction filtered and dried in vacuo. 4.65 g (80%) of an orange red solid melting at 154°–157° C. are obtained.

$C_{15}H_{19}N_5O_3S$ (349.41)
Rf=0.39 (Solvent F)

c) $N^1$-[3-(1H-Imidazol-4-yl)propyl]-$N^2$-tert.-butoxycarbonyl-$N^3$-[1-[4-(6-methyl-2-oxo-3,6-dihydro-1,3,4-thiadiazin-5-yl)-2-nitro-phenyl]piperidin-4-yl]-guanidine 1.00 g (2.86 mmol) of the amine obtained under b) is stirred together with 0.90 g (2.87 mmol) of N-(tert.-butoxycarbonyl)-imidocarbonic acid diphenylester in 20 ml of acetonitrile for 2 hours at room temperature.

0.36 g (2.86 mmol) of 3-(1H-imidazol-4-yl)-propylamine are added and the reaction mixture is boiled under reflux for 12 hours. The cooled solution is concentrated by evaporation in vacuo and the residue is chromatographed on silica gel with solvent H. After concentration by evaporation in vacuo, the product fractions yield an orange coloured foam which crystallises after it has been boiled up with 20 ml of acetonitrile.

0.84 g (49%) of orange yellow crystals, m.p. 221°–223° C.

$C_{27}H_{37}N_9O_5S$ (599.72)
Rf=0.5 (Solvent H)

| $^1$H-NMR data | δ = | 1.38 | (s) | 9H |
|---|---|---|---|---|
| (DMSO-$d_6$, TMS as internal standard) | | 1.46 | (d) | 3H |
| | | 1.5–2.0 | (m) | 6H |
| | | 2.50 | (t) | 2H |
| | | 2.9–3.4 | (m) | 7H |
| | | 4.79 | (q) | 1H |
| | | 6.78 | (s) | 1H |
| | | 7.37 | (d) | 1H |
| | | 7.52 | (s) | 1H |
| | | 7.96 | (dd) | 1H |
| | | 8.20 | (d) | 1H |
| | | 9.00 | (broad) | 2H, replaceable by $D_2O$, ppm. |

EXAMPLE 5

5-[4-[4-[3-(1H-Imidazol-4-yl)propylamino-(tert.-butoxycarbonyl)-iminomethylene]-piperazin-1-yl]-3-nitro-phenyl]-6-methyl-3H,6H-1,3,4-thiadiazin-2-one

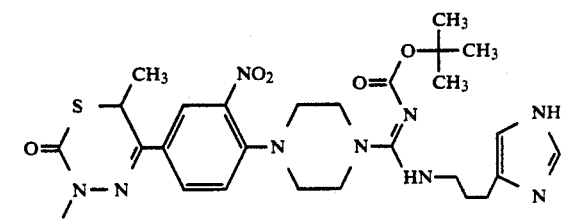

9.0 g (26.8 mmol) of 6-Methyl-5-[4-(piperazin-1-yl)-3-nitro-phenyl]-3H,6H-1,3,4. thiadiazin-2-one and 8.4 g (26.8 mmol) of N-(tert.-butoxycarbonyl)-imidocarbonic acid diphenylester are stirred into 60 ml of acetonitrile for 16 hours at room temperature. After the addition of 3.4 g (26.8 mmol) of 3-(1H-imidazol-4-yl)-propylamine, the reaction mixture is boiled under reflux for 8 hours. The oil obtained after removal of the solvent by evaporation in vacuo is chromatographed on silica gel with solvent G.

10.2 g (65%) of an orange yellow, amorphous solid is obtained from the main fraction after concentration by evaporation in vacuo.

$C_{26}H_{35}N_9O_5S$ (585.69)
Rf=0.3 (Solvent H)

| $^1$H-NMR data (DMSO-$d_6$, TMS as internal standard) | δ = | 1.37 | (s) | 9H |
|---|---|---|---|---|
| | | 1.47 | (d) | 3H |
| | | 1.78 | (m) | 2H |
| | | 2.45–2.6 | (m) | 2H |
| | | 3.0–3.55 | (m) | 10H |
| | | 4.80 | (q) | 1H |
| | | 6.74 | (s) | 1H |
| | | 7.37 | (d) | 1H |
| | | 7.53 | (s) | 1H |
| | | 7.99 | (dd) | 1H |
| | | 8.24 | (d) | 1H |
| | | 11.76 | (s) | 1H, replaceable by D$_2$O ppm. |

EXAMPLE 6

3-Cyano-5-[4-[4-[3-(1H-imidazol 4-yl)propylamino-(tert.butoxycarbonyl)iminomethylene]-piperazin-1-yl]-phenyl]-6-methyl-3H.6H-1,3,4-thiadiazin-2-one

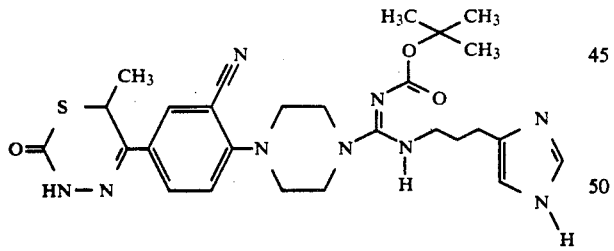

1.5 g (4.8 mmol) of 5-[3-Cyano-4-(piperazin-1-yl)phenyl]-6-methyl-3H,6H-1,3,4-thiadiazin-2-one and 1.5 g (4.8 mmol) of N-(tert.-butoxycarbonyl) imidocarbonic acid diphenylester are stirred in 25 ml of acetonitrile for 6 hours at 40° C.

0.6 g (4.8 mmol) of 3-(1H-imidazol-4-yl)-propylamine are added and the reaction mixture is boiled under reflux for 9 hours. The crude product obtained after removal of the solvent by evaporation in vacuo is chromatographically purified on silica gel, first with solvent G and then a second time with solvent H.

0.35 g (13%) of the title compound is obtained in the form of a beige coloured, amorphous solid.

$C_{27}H_{35}N_9O_3S$ (565.70)
Rf=0.5 (Solvent A)

| $^1$H NMR data (DMSO-$d_6$, TMS as internal standard) | δ = | 1.37 | (s) | 9H |
|---|---|---|---|---|
| | | 1.46 | (d) | 3H |
| | | 1.78 | (m) | 2H |
| | | 2.51 | (t) | 2H |
| | | 3.0–3.6 | (m) | 10H |
| | | 4.77 | (q) | 1H |
| | | 6.73 | (s) | 1H |
| | | 7.24 | (d) | 1H |
| | | 7.51 | (s + broad) | 2H 1H replaceable by D$_2$O |
| | | 8.03 | (dd) | 1H |
| | | 8.10 | (d) | 1H |
| | | 11.78 | (s) | 1H replaceable by D$_2$O ppm. |

EXAMPLE 7

$N^1$-[3-(1H-Imidazol-4-yl)propyl]-$N^3$-[1-[4-(6-methyl-2-oxo-3,6-dihydro-1,3,4-thiadiazin-5-yl)-2-nitro-phenyl]-piperidin-4-yl]-guanidine

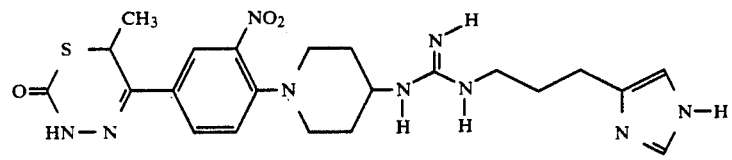

1.7 g (2.8 mmol) of $N^1$-[3-(1H-imidazol-4-yl)propyl]-$N^2$-tert.-butoxycarbonyl-$N^3$-[1-[4 (6-methyl-2-oxo-3,6-dihydro-1,3,4-thiadiazin-5-yl)-2-nitro-phenyl]-piperidin-4-yl]-guanidine (Example 4) are dissolved in 50 ml of dichloromethane. 2.1 ml (28 mmol) of trifluoroacetic acid are added and the reaction mixture is stirred for 2 days at room temperature. The solvent is then removed by evaporation in vacuo at 20° C and the residue is taken up in 10 ml of saturated potassium carbonate solution and extracted with 3×10 ml of isopropanol. The combined organic phases are concentrated by evaporation and the residue is chromatographed twice on silica gel, first with solvent F and then with solvent E.

The product fractions are in each case concentrated by evaporation, taken up in saturated potassium carbonate solution and extracted three times with isopropanol.

The solid obtained after drying and concentration of the combined organic phases by evaporation is stirred into 20 ml of water, suction filtered and recrystallised from 45 ml of ethanol. 0.72 g (51%) of an orange red solid, m.p. 193°–195° C., is obtained.

$C_{22}H_{29}N_9O_3S$ (499.60)
Rf=0.36. (Solvent E)

| $^1$H-NMR data (DMSO-$d_6$, TMS as internal standard) | δ = | 1.33 | (d) | 3H |
|---|---|---|---|---|
| | | 1.5–2.0 | (m) | 6H |
| | | 2.55 | (t) | 2H |
| | | 2.8–3.7 | (m) | 7H |
| | | 4.44 | (q) | 1H |
| | | 6.77 | (s) | 1H |
| | | 7.27 | (d) | 1H |
| | | 7.53 | (s) | 1H |
| | | 7.96 | (dd) | 1H |
| | | 8.0 | (broad) | 4H replaceable by D$_2$O |
| | | 8.10 | (d) | 1H ppm. |

EXAMPLE 8

5-[4-[4-[3-(1H-Imidazol-4-yl)propylamino-(tert.-butoxycarbonyl)-iminomethylene]-piperazin-1-yl]-3-nitro-phenyl]-6H-1,3,4-thiadiazin-2-one

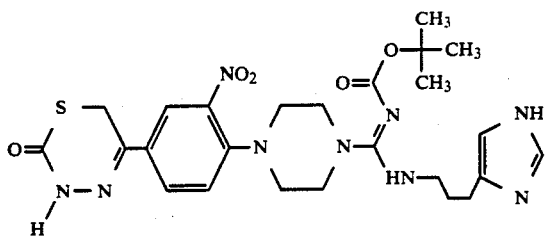

Starting from 4.0 g (12.5 mmol) of 5-4-(piperazin-1-yl)-3-nitro phenyl]-3H.6H-1,3,4-thiadiazin-2-one, 3.9 g (12.5 mmol) of N-(tert.-butoxycarbonyl)-imidocarbonic acid diphenylester and 1.56 g (12.5 mmol) of 3-(1H-imidazol-4-yl)propylamine, 1.5 g (21%) of an orange yellow, amorphous solid are obtained in a manner analogous to Example 5 after chromatographic purification with solvent C.

$C_{25}H_{33}N_9O_5S$ (571.66)

| $^1$H-NMR data (DMSO-$d_6$, TMS as internal standard) | δ = | 1.36 | (s) | 9H |
|---|---|---|---|---|
| | | 1.77 | (quin) | 2H |
| | | 2.50 | (t) | 2H |
| | | 2.9–3.7 | (m) | 10H |
| | | 4.24 | (s) | 2H |
| | | 6.73 | (s) | 1H |
| | | 7.37 | (d) | 1H |
| | | 7.51 | (s) | 1H |
| | | 7.98 | (dd) | 1H |
| | | 8.24 | (d) | 1H |
| | | 11.65 | (s) | 1H, replaceable by D$_2$O |
| | | 11.8 | (broad) | 2H, replaceable by D$_2$O ppm. |

EXAMPLE 9

5-[4-[4-[3-(1H-Imidazol-4-yl)propylamino-iminomethylene]piperazin-1-yl]-3-nitro-phenyl]-3H,6H-1,3,4-thiadiazin-2-one

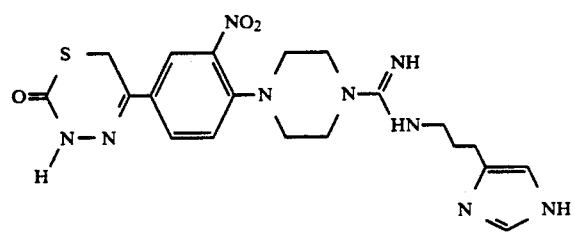

0.78 g (32%) of an orange, amorphous solid is obtained by a method analogous to that of Example 7 from 3.0 g (5.2 mmol) of 5-[4-[4-[3-(1H-imidazol-4-yl)propylamino(tert.-butoxycarbonyl)iminomethylene]-piperazin-1yl-]-3-nitro-phenyl]-3H,6H-1,3,4-thiadiazin-2-one (Example 8).

$C_{20}H_{25}N_9O_3S$ (471.54)

Rf=0.4 (Solvent B)

| $^1$H-NMR data (CD$_3$OD, TMS as internal standard) | δ = | 1.89 | (quin) | 2H |
|---|---|---|---|---|
| | | 2.64 | (t) | 2H |
| | | 3.0–3.7 | (m) | 10H |
| | | 4.13 | (s) | 2H |
| | | 4.9 | (broad) | 4H, replaceable by D$_2$O |
| | | 6.82 | (s) | 1H |
| | | 7.31 | (d) | 1H |
| | | 7.62 | (s) | 1H |
| | | 7.99 | (dd) | 1H |
| | | 8.24 | (d) | 1H ppm. |

EXAMPLE 10

$N^1$-[3-(1H-Imidazol-4-yl)propyl]-$N_2$-tert.butoxycarbonyl-$N^3$-[1-[4-(2-oxo-3,6-dihydro-1,3,4-thiadiazin-5-yl)-2-nitro-phenyl]-piperidin-4-yl]-guanidine

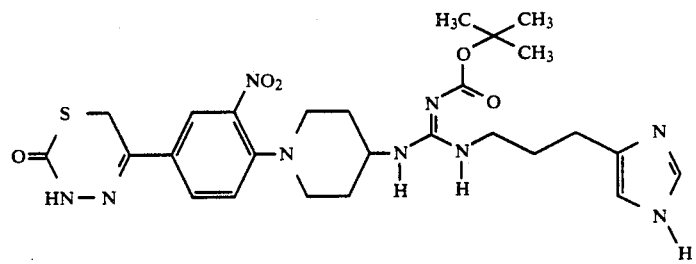

1.0 g (2.98 mmol) of 5-[4-(4-aminopiperidin.1-yl)-3-nitro-phenyl]-3H,6H-1,3,4-thiadiazin-2-one, 0.93 g (2.98 mmol) of N-(tert..butoxycarbonyl)-imidocarbonic acid diphenylester and 0.37 g (2.98 mmol) of 3-(1H-imidazol-4-yl)propylamine in 20 ml of dimethylformamide are reacted by a method analogous to that of Example 4c) to yield 0.65 g (37%) of an orange yellow solid after chromatography on silica gel with Solvent H $C_{26}H_{35}N_9O_5S$ (585.69)

Rf=0.45 (Solvent H)

| $^1$H-NMR data (DMSO-$d_6$, TMS as internal standard) | δ = | 1.37 | (s) | 9H |
|---|---|---|---|---|
| | | 1.5–2.0 | (m) | 6H |
| | | 2.50 | (t) | 2H |
| | | 2.9–3.4 | (m) | 7H |
| | | 4.22 | (s) | 2H |
| | | 6.77 | (s) | 1H |
| | | 7.37 | (d) | 1H |
| | | 7.51 | (s) | 1H |
| | | 7.96 | (dd) | 1H |
| | | 8.23 | (d) | 1H |
| | | 11.75 | (s) | 1H, replaceable by D$_2$O |
| | | 11.8 | (broad) | 2H, replaceable by D$_2$O ppm. |

EXAMPLE 11

5-[4-[1-[3-(1H-Imidazol-4-yl)propylamino-(tert.-butoxycarbonyl)iminomethylene]-piperidin-4-yl]- amino-3-nitrophenyl]-6-methyl-3H,6H-1,3,4-thiadiazin-2-one

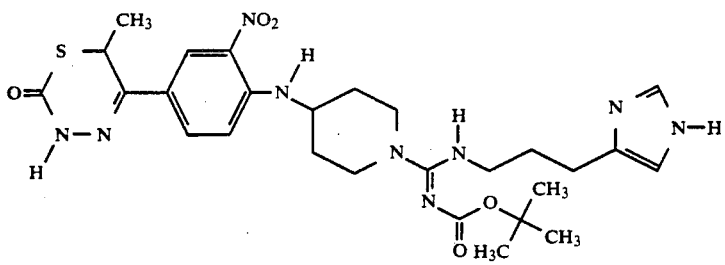

a) 5-[4-[1-[Phenoxy-(tert.-butoxycarbonyl)iminomethylene]piperidin-4-yl]amino-3-nitrophenyl]-6.methyl-3H,6H-1,3,4-thiadiazin-2-one 0.80 g (2.28 mmol) of 5-[4-(piperidin-4-yl)amino-3-nitrophenyl]-6-methyl-3H,6H-1,3,4-thiadiazin-2-one and 0.80 g (2.53 mmol) of N-tert.-butoxycarbonyl-diphenylimidocarbonate are boiled under reflux in 30 ml of acetonitrile for 2 hours. After removal of the solvent by evaporation in vacuo, the crude product obtained is chromatographed on silica gel with Solvent H. Concentration of the main fraction by evaporation in vacuo gives rise to an orange yellow foam which is stirred up with methanol to yield 0.80 g (62%) of orange crystals melting at 207°–208° C..

$C_{27}H_{32}N_6O_6S$ (568.66)
Rf=0.68 (Solvent H)

b) 5-[4-[1-[3-(1H-Imidazol-4-yl)-propylamino-(tert.-butoxycarbonyl)iminomethylene]-piperidin-4-yl]amino-3-nitro-phenyl]6-methyl-3H,6H-1,3,4-thiadiazin-2-one 0.75 g (1.31 mmol) of the compound obtained under a) are heated to reflux for 10 hours with 0.17 g (1.35 mmol) of 3-(1H-imidazol-4-yl)propylamine in 30 ml of acetonitrile. After cooling, the solution is concentrated by evaporation in vacuo and the residue is purified on silica gel with Solvent H. The main fraction having the Rf-value 0.37 yields 0.43 g (55%) of an orange yellow, amorphous solid after concentration by evaporation in vacuo.

$C_{27}H_{37}N_9O_5S$ (599.72)
Rf=0.37 (Solvent H)

| $^1$H-NMR data (DMSO-d$_6$, TMS as internal standard) | δ = | 1.37 | (s) | 9H |
|---|---|---|---|---|
| | | 1.46 | (d) | 3H |
| | | 1.5–2.1 | (m) | 6H |
| | | 2.51 | (t) | 2H |
| | | 2.9–3.2 | (m) | 4H |
| | | 3.7–4.0 | (m) | 3H |
| | | 4.81 | (q) | 1H |
| | | 6.73 | (s) | 1H |
| | | 7.33 | (d) | 1H |
| | | 7.50 | (s) | 1H |
| | | 7.99 | (dd) | 1H |
| | | 8.17 | (d) | 1H, replaceable by D$_2$O |
| | | 8.47 | (d) | 1H |
| | | 11.67 | (s) | 1H, replaceable by D$_2$O ppm. |

EXAMPLE 12

5-[4-[1-[3-(1H-Imidazol-4-yl)propylamino-iminomethylene]piperidin-4-yl]amino-3-nitrophenyl]3H,6H-1,3,4-thiadiazin-2-one

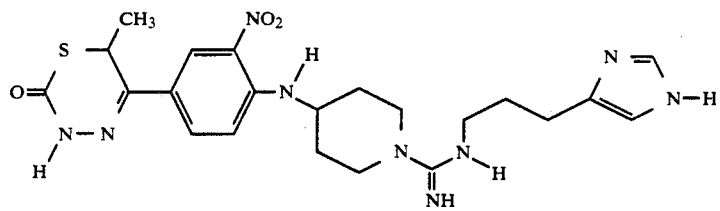

0.43 g (0.71 mmol) of 5-[4-[1-[3-(1H-imidazol-4-yl)-propylamino-(tert.-butoxycarbonyl)-iminomethylene]-piperidin-4-yl]amino-3-nitrophenyl]-6-methyl-3H,6H-1,3,4-thiadiazin-2-one are reacted with trifluoroacetic acid in dichloromethane by a method analogous to that of Example 7 to yield 28 g (79%) of a yellowish orange, amorphous solid after chromatographic purification with Solvent C.

$C_{22}H_{29}N_9O_3S$ (499.60)
Rf=0.42 (Solvent F)

| $^1$H-NMR data (DMSO-d$_6$-TMS as internal standard) | δ = | 1.43 | (d) | 3H |
|---|---|---|---|---|
| | | 1.4–2.05 | (m) | 6H |
| | | 2.54 | (t) | 2H |
| | | 2.8–3.1 | (m) | 4H |
| | | 3.7–4.0 | (m) | 3H |
| | | 4.70 | (q) | 1H |
| | | 6.71 | (s) | 1H |
| | | 7.29 | (d) | 1H |
| | | 7.50 | (s) | 1H |
| | | 7.7 | (broad) | 4H replaceable by D$_2$O |
| | | 8.01 | (dd) | 1H |
| | | 8.17 | (d) | 1H, replaceable by D$_2$O |
| | | 8.43 | (d) | 1H ppm. |

EXAMPLE 13

3-[4-[4-[3-(1H-Imidazol-4 yl)propylamino-iminomethylene]-piperazin-1-yl]-3-nitrophenyl]-4,5-dihydro-1,2,4-triazin-6(1H)-one

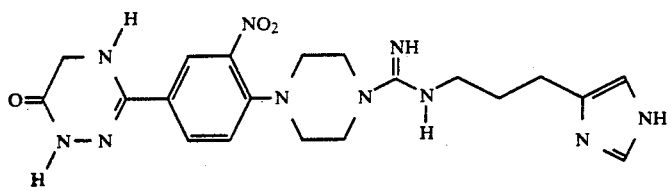

0.23 g (1.83 mmol) of 3.(1H-imidazol-4-yl)-propylamine are added to a suspension of 0.85 g (1.68 mmol) of 3-[4-[4-(methylthioiminomethylene)-piperazin-1-yl]-3-nitrophenyl]-4,5-dihydro-1,2,4-triazin-6(1H)-one in 20 ml of DMF and the reaction mixture is stirred at 50° C. for 36 hours. The resulting precipitate is suction filtered, dried and chromatographed on silica gel with methanol/dichloromethane/conc.ammonia in a ratio of 10:5:2 as solvent. The pure product fractions (Rf=0.43) are combined and concentrated by evaporation in vacuo. The residue obtained is crystallised with absolute ethanol and yields 0.26 g (25%) of an orange yellow, amorphous solid.

$C_{20}H_{26}N_{10}O_3$ (454.50)

Rf=0.43 (Solvent1 methanol/dichloromethane/conc. ammonia 10:5:2)

| $^1$H-NMR data (DMSO-$d_6$, TMS as internal standard) | δ = 1.84 | (quin) | 2H |
|---|---|---|---|
| | 2.56 | (t) | 2H |
| | 3.0–3.8 | (m) | 12H |
| | 6.78 | (s) | 1H |
| | 7.23 | (d) | 1H |
| | 7.55 | (s) | 1H |
| | 8.02 | (dd) | 1H |
| | 8.1 | (broad) | 2H, replaceable by $D_2O$ |
| | 8.35 | (d) | 1H |
| | 8.6 | (broad) | 3H, replaceable by $D_2O$ ppm. |

We claim:

1. A compound having the formula

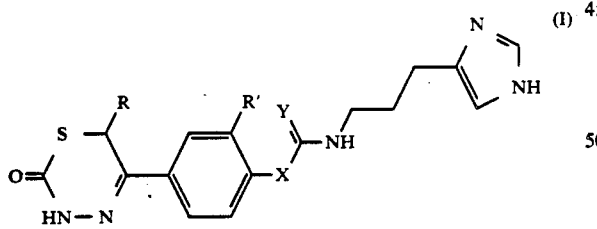
(I)

wherein R is hydrogen, $C_1$-$C_3$ alkyl or hydroxymethyl; R' is hydrogen, nitro, cyano or halogen; X is selected from the group consisting of

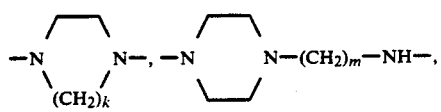

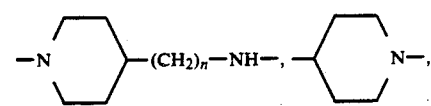

-continued

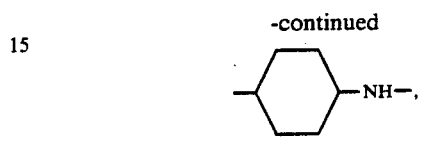

$-NH(CH_2)_m-NH-$, $-O(CH_2)_n-NH-$ and $-(CH_2)_n-NH-$, wherein k is 2 or 3, m is 2, 3, 4, 5 or 6 and n is 0, 1, 2, 3 or 4; and =Y is =O, =NH, $$=N-\underset{\underset{O}{\|}}{C}-R^1 \text{ or } =N-\underset{\underset{O}{\|}}{C}-OR^2,$$

wherein $R^1$ is phenyl or naphthyl optionally substituted with one or more halogen, $C_1$-$C_3$ alkyl or $C_1$-$C_3$ alkoxy, and $R^2$ is straight chain or branched chain $C_1$-$C_4$ alkyl optionally substituted with one or more halogen, $C_1$-$C_3$ alkoxy or phenyl; or a physiologically acceptable salt thereof.

2. A compound according to claim 1, wherein =Y is =NH, $$=N-\underset{\underset{O}{\|}}{C}-R^1 \text{ or } =N-\underset{\underset{O}{\|}}{C}-OR^2$$

wherein $R^1$ and $R^2$ are as defined in claim 10, or a physiologically acceptable salt thereof.

3. A compound having the formula

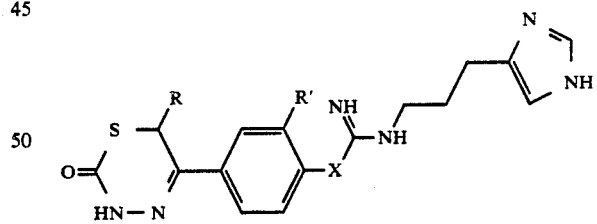

wherein R is hydrogen, $C_1$-$C_3$ alkyl or hydroxymethyl; R' is hydrogen, nitro, cyano or halogen; and X is selected from the group consisting of

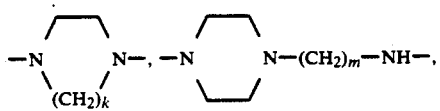

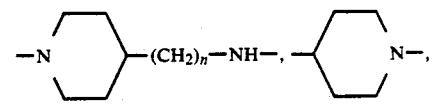

-continued

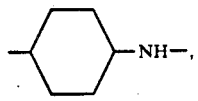

—NH(CH$_2$)$_m$—NH—, —O(CH$_2$)$_n$—NH— and —(CH$_2$)$_n$—NH—, wherein k is 2 or 3, m is 2, 3, 4, 5 or 6 and n is 0, 1, 2, 3 or 4; or a physiologically acceptable salt thereof.

4. A compound according to claim 1, wherein R is methyl.

5. A compound according to claim 1, wherein R' is nitro or cyano.

6. A compound according to claim 1, wherein X is

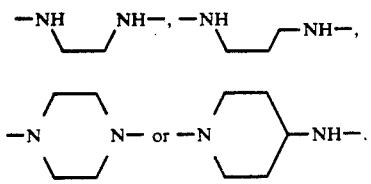

7. The compound according to claim 1, which is:
N$^1$-[3-(1H-imidazol-4-yl)propyl]-N$^3$-[2-[[4-(6-methyl-2-oxo-3,6-dihydro-1,3,4-thiadiazin-5-yl)-2-nitrophenyl]amino]ethyl]-guanidine;
N$^1$-[3-(1H-imidazol-4-yl)propyl]-N$^3$-[3-[[4-(6-methyl-2-oxo-3,6-dihydro-1,3,4-thiadiazin-5-yl)-2-nitrophenyl]amino]propyl]-guanidine;
5-[4-[4-[3-(1H-imidazol-4-yl)propylamino-iminomethylene]piperazin-1-yl]-3-nitro-phenyl]-6-methyl-3H,6H-1,3,4-thiadiazin-2-one;
N$^1$-[3-(1H-imidazol-4-yl)propyl]-N$^2$-tert.-butoxycarbonyl-N$^3$-[1-[4-(6-methyl-2-oxo-3,6-dihydro-1,3,4-thiadiazin-5-yl)-2-nitro-phenyl]-piperidin-4-yl]-guanidine;
5-[4-[4-[3-(1H-imidazol-4-yl)propylamino-(tert.-butoxycarbonyl)-iminomethylene]-piperazin-1-yl]-3-nitro-phenyl]-6-methyl-3H,6H-1,3,4-thiadiazin-2-one;
3-cyano-5-[4-[4-[3-(1H-imidazol-4-yl)propylamino-(tert.-butoxycarbonyl)iminomethylene]-piperazin-1-yl]-phenyl]-6-methyl-3H,6H-1,3,4-thiadiazin-2-one;
N$^1$-[3-(1H-imidazol-4-yl)propyl]-N$^3$-[1-[4-(6-methyl-2-oxo-3,6-dihydro-1,3,4-thiadiazin-5-yl)-2-nitrophenyl]-piperidin-4-yl]-guanidine;
5-[4-[4-[3-(1H-imidazol-4-yl)propylamino-(tert.butoxycarbonyl)-iminomethylene]-piperazin-1-yl]-3-nitrophenyl]-3H,6H-1,3,4-thiadiazin-2-one;
5-[4-[4-[3-(1H-imidazol-4-yl)propylamino-iminomethylene]piperazin-1-yl]-3-nitro-phenyl]-3H,6H-1,3,4-thiadiazin-2-one;
N$^1$-[3-(1H-imidazol-4-yl)propyl]-N$^2$-tert.-butoxycarbonyl-N$^3$-[1-[4-(2-oxo-3,6-dihydro-1,3,4-thiadiazin-5-yl)-2-nitrophenyl]-piperidin-4-yl]-guanidine;
5-[4-[1-[3-(1H-imidazol-4-yl)propyamino-(tert.butoxycarbonyl)iminomethylene]-piperidin-4-yl]-amino-3-nitrophenyl]-6-methyl-3H,6H-1,3,4-thiadiazin-2-one; or
5-[4-[1-[3-(1H-imidazol-4-yl)propylamino-iminomethylene]piperidin-4-yl]amino-3-nitrophenyl]-3H,6H-1,3,4-thiadiazin-2-one;
or a physiologically acceptable salt thereof.

8. 5-[4-[4-[3-(1H-Imidazol-4-yl)-propylamino-iminomethylene]-piperazin-1-yl]-3-nitro-phenyl]-6-methyl-3H,6H-1,3,4-thiadiazin-2-one and the physiologically acceptable salts thereof.

9. N$^1$-[3-(1H-Imidazol-4-yl)propyl]-N$^3$-[1-[4(6-methyl-2-oxo-3,6-dihydro-1,3,4-thiadiazin-5-yl)-2-nitrophenyl]piperidin-4-yl]-guanidine and the physiologically acceptable salts thereof.

10. A pharmaceutical composition of matter, in unit dosage form, for use in the treatment or prevention of heart or circulatory disease in a warm-blooded animal, said composition comprising, per dosage unit, a cardiotonically effective amount of a compound as defined in claim 1 or a physiologically acceptable salt thereof, and a pharmaceutically acceptable carrier therefor.

11. A pharmaceutical composition of matter, in unit dosage form, for use in the treatment or prevention of heart or circulatory disease in a warm-blooded animal, said composition comprising, per dosage unit, a cardiotonically effective amount of a compound as defined in claim 3 or a physiologically acceptable salt thereof, and a pharmaceutically acceptable carrier therefor.

12. A pharmaceutical composition of matter, in unit dosage form, for use in the treatment or prevention of heart or circulatory disease in a warm-blooded animal, said composition comprising, per dosage unit, a cardiotonically effective amount of a compound as defined in claim 7 or a physiologically acceptable salt thereof, and a pharmaceutically acceptable carrier therefor.

13. A pharmaceutical composition of matter, in unit dosage form, for use in the treatment or prevention of heart or circulatory disease in a warm-blooded animal, said composition comprising, per dosage unit, a cardiotonically effective amount of a compound as defined in claim 8 or a physiologically acceptable salt thereof, and a pharmaceutically acceptable carrier therefor.

14. A pharmaceutical composition of matter, in unit dosage form, for use in the treatment or prevention of heart or circulatory disease in a warm-blooded animal, said composition comprising, per dosage unit, a cardiotonically effective amount of a compound as defined in claim 9 or a physiologically acceptable salt thereof, and a pharmaceutically acceptable carrier therefor.

15. A method for the treatment or prevention of heart or circulatory disease in a warm-blooded animal in need of same, said method comprising administering to said animal a cardiotonically effective amount of a compound as defined in claim 1 or a physiologically acceptable salt thereof.

16. A method for the treatment or prevention of heart or circulatory disease in a warm-blooded animal in need of same, said method comprising administering to said animal a cardiotonically effective amount of a compound as defined in claim 3 or a physiologically acceptable salt thereof.

17. A method for the treatment or prevention of heart or circulatory disease in a warm-blooded animal in need of same, said method comprising administering to said animal a cardiotonically effective amount of a compound as defined in claim 7 or a physiologically acceptable salt thereof.

18. A method for the treatment or prevention of heart or circulatory disease in a warm-blooded animal in need of same, said method comprising administering to said animal a cardiotonically effective amount of a compound as defined in claim 8 or a physiologically acceptable salt thereof.

19. A method for the treatment or prevention of heart or circulatory disease in a warm-blooded animal in need of same, said method comprising administering to said animal a cardiotonically effective amount of a compound as defined in claim 9 or a physiologically acceptable salt thereof.

* * * * *